US005830736A

United States Patent [19]
Oxenbøll et al.

[11] Patent Number: 5,830,736
[45] Date of Patent: Nov. 3, 1998

[54] LIPOLYTIC ENZYME

[75] Inventors: Karen Margrethe Oxenbøll, Charlottenlund; Kim Borch, Copenhagen K; Shamkant Anant Patkar, Lyngby, all of Denmark

[73] Assignee: Novo Nordisk A/S, Bagsvaerd, Denmark

[21] Appl. No.: 809,426

[22] PCT Filed: Oct. 26, 1995

[86] PCT No.: PCT/DK95/00425

§ 371 Date: Apr. 4, 1997

§ 102(e) Date: Apr. 4, 1997

[87] PCT Pub. No.: WO96/13579

PCT Pub. Date: May 9, 1996

[30] Foreign Application Priority Data

Oct. 26, 1994 [DK] Denmark .............................. 1235/94

[51] Int. Cl.[6] .............................. C12N 9/20; C11D 3/386

[52] U.S. Cl. .............................. 435/198; 510/392

[58] Field of Search .............................. 435/198; 510/392

[56] References Cited

U.S. PATENT DOCUMENTS 5,439,811 8/1995 Yamashita et al. .................. 435/91.53

FOREIGN PATENT DOCUMENTS 130 064 1/1985 European Pat. Off. .
WO 94/03578 2/1994 WIPO .

OTHER PUBLICATIONS

Nagao, et al., J. Biochem, vol. 116, pp. 536–540 (Mar. 7, 1994).

Igumenov, et al., Prikl Biochem, vol. 18(5), pp. 652–658 (1982).

Lin, et al., Physiological Plant Pathology, vol. 17, pp. 1–15 (1980).

Soliday, et al., Archives of Biochemistry & Biophysics, vol. 176, pp. 334–343 (Feb. 25, 1976).

Ohkouchi et al., (1993) SEN–I Gakkaishi 49(4), 182–189.

Nakanishi et al., SEN–I Gakkaishi, vol. 49, No. 11, pp. 586–593 (1993).

P.E. Kolattukudy, Institute of Biological Chemistry and Biochemistry/Biophysics Program, From "Lipases", Borgstrom, et al, Editors (1984) pp. 471–504.

Nakanishi. S., et al. (1994) Chemical Abstracts 120:211249x.

*Primary Examiner*—Charles L. Patterson, Jr.
*Attorney, Agent, or Firm*—Steve T. Zelson; James Harrington

[57] ABSTRACT

The present invention relates to novel lipolytic enzymes. More specifically the invention provides novel lipolytic enzymes having the properties of a lipase native to the strain *Fusarium culmorum* CBS 513.94, or has immunochemical properties identical or partially identical to those of a lipase native to the strain *Fusarium culmorum* CBS 513.94.

11 Claims, 1 Drawing Sheet

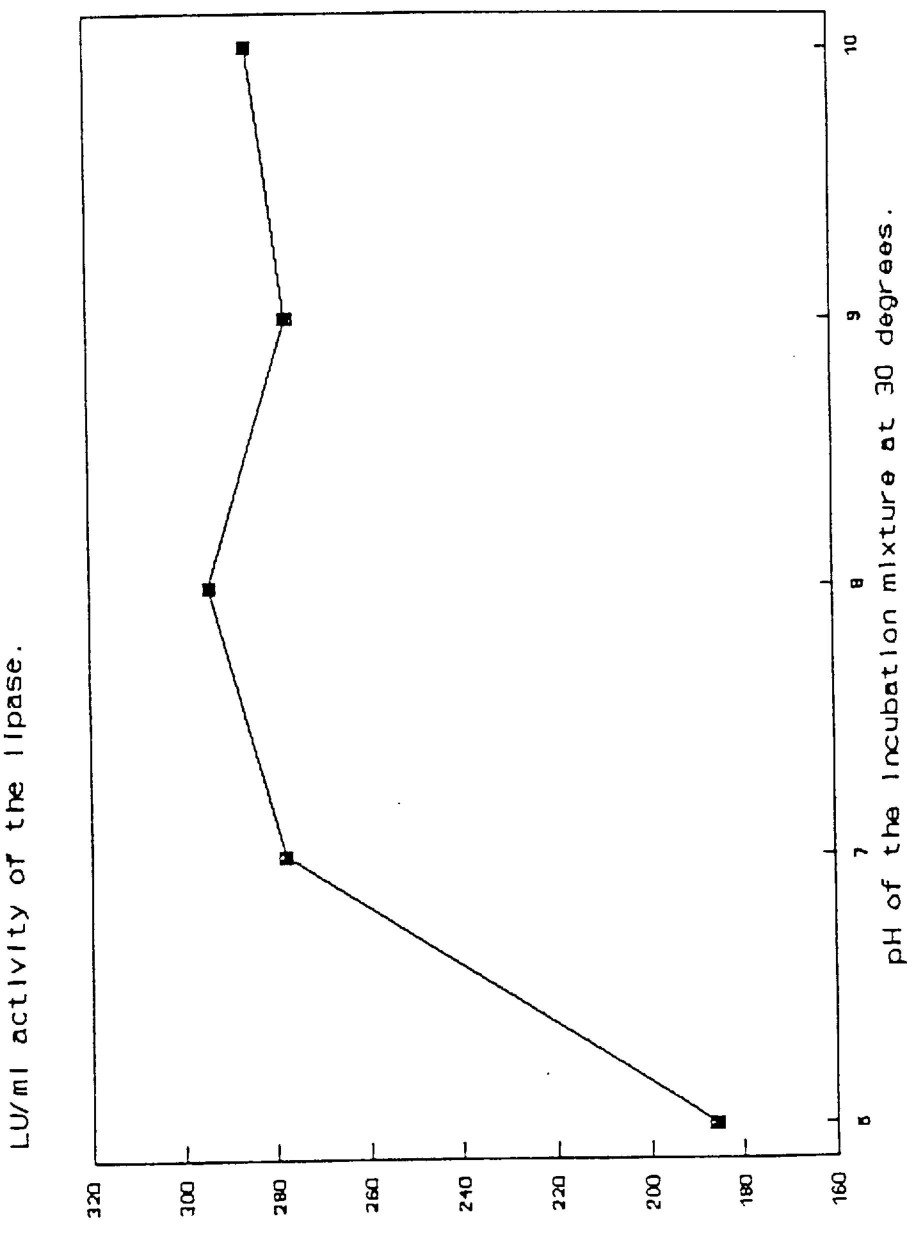
FIG. I

LIPOLYTIC ENZYME

CROSS-REFERENCE TO RELATED APPLICATIONS

This application is a 35 U.S.C. 371 national application of PCT/DK95/00425 filed Oct. 26, 1995 and claims priority under 35 U.S.C. 119 of Danish application 1235/94 filed Oct. 26, 1994, the contents of which are fully incorporated herein by reference.

TECHNICAL FIELD

The present invention relates to novel lipolytic enzymes. More specifically the invention provides novel lipolytic enzymes having the properties of a lipase native to the strain *Fusarium culmorum* CBS 513.94, or has immunochemical properties identical or partially identical to those of a lipase native to the strain *Fusarium culmorum* CBS 513.94.

BACKGROUND ART

Lipolytic enzymes find multiple industrial applications. Alkaline lipases are of particular interest for use in detergent compositions.

Alkaline lipases of microbial origin have been described, including lipases obtained from Fusarium. However, lipases obtained from *Fusarium culmorum* have never been disclosed.

SUMMARY OF THE INVENTION

It is an object of the present invention to provide novel alkaline lipolytic enzymes (EC 3.1.1.3).

Accordingly, in its first aspect, the invention provides lipolytic enzymes having immunochemical properties identical or partially identical to those of a lipase obtained from the strain *Fusarium culmorum* CBS 513.94.

In its second aspect, the invention provides a process for the preparation of the lipolytic enzyme, which process comprises cultivation of a lipase producing strain of *Fusarium culmorum* in a suitable nutrient medium, containing carbon and nitrogen sources and other inorganic salts, followed by recovery of the lipolytic enzyme.

In its third aspect, the invention provides a process for the preparation of a lipolytic enzyme according to any of claims 1–6, which process comprises isolating a DNA fragment encoding the lipolytic enzyme; combining the DNA fragment with an appropriate expression signal in an appropriate plasmid vector; introducing the plasmid vector into an appropriate host either as an autonomously replicating plasmid or integrated into the chromosome; cultivating the host organism under conditions leading to expression of the lipolytic enzyme; and recovering of the enzyme from the culture medium.

In further aspects, the invention provides detergent compositions, as well as a detergent additives, comprising the lipolytic enzyme of the invention.

Finally, the invention provides a biologically pure culture of the strain *Fusarium culmorum* CBS 513.94.

BRIEF DESCRIPTION OF THE DRAWINGS

FIG. 1 show the relation between pH and lipase activity of the lipolytic enzyme of the present invention determined at 30° C. in the range of from pH 6 to pH 10.

DETAILED DISCLOSURE OF THE INVENTION

The present invention provides novel lipolytic enzymes having the properties of a lipase native to the strain *Fusarium culmorum* CBS 513.94.

The Microorganism

The invention provides lipolytic enzymes derived from a strain of the fungus *Fusarium culmorum. Fusarium culmorum* is a known species and strains of *Fusarium culmorum* have been deposited and are publicly available from depositary institutes, e.g. Deutsche Sammlung von Mikroorganismen und Zellkulturen GmbH (DSM), Germany, and American Type Culture Collection (ATCC), U.S.A.

In a preferred embodiment the invention provides a lipolytic enzyme derived from the strain *Fusarium culmorum* DSM 1094, *Fusarium culmorum* DSM *Fusarium culmorum* 62184, *Fusarium culmorum* DSM 62188, *Fusarium culmorum* DSM 62191, *Fusarium culmorum* DSM 62223, *Fusarium culmorum* ATCC 12656, *Fusarium culmorum* ATCC 15620, *Fusarium culmorum* ATCC 16430, *Fusarium culmorum* ATCC 16551, *Fusarium culmorum* ATCC 26556, *Fusarium culmorum* ATCC 34910, *Fusarium culmorum* ATCC 34913, *Fusarium culmorum* ATCC 36017, *Fusarium culmorum* ATCC 36879, *Fusarium culmorum* ATCC 36881, *Fusarium culmorum* ATCC 36886, *Fusarium culmorum* ATCC 44417, *Fusarium culmorum* ATCC 46040, *Fusarium culmorum* ATCC 56088, *Fusarium culmorum* ATCC 56089, *Fusarium culmorum* ATCC 60275, *Fusarium culmorum* ATCC 60362, *Fusarium culmorum* ATCC 62214, *Fusarium culmorum* ATCC 62215, or *Fusarium culmorum* ATCC 64075, or a mutant or a variant thereof.

In its most preferred embodiment the invention provides a lipolytic enzyme derived from the strain *Fusarium culmorum* CBS 513.94, or a muant or a variant thereof. This strain has been deposited according to the Budapest Treaty on the International Recognition of the Deposit of Microorganisms for the Purposes of Patent Procedure at Centraalbureau Voor Schimmelcultures (CBS), Oosterstraat 1, Postbus 273, NL-3740 AG Baarn, Netherlands, on 25 Oct. 1994.

In another aspect, the invention provides a biologically pure culture of the strain *Fusarium culmorum* CBS 513.94.

Physico-Chemical Properties

In preferred embodiments, the lipolytic enzyme of the invention may be characterized by having one or more of the following physico-chemical properties.

The enzyme has a pH optimum in the range of from about 7 to about pH 9, more specifically around pH 8, when determined at 30° C. with tributyrine as substrate.

The enzyme has the following N-terminal amino acid sequence (cf. SEQ ID NO:1):

Ala—Val—Ser—Val—Ser—Thr—Thr—Asp—Phe—Gly—Asn—
Phe—Lys—Phe—Tyr—Ile—Gln—His—Gly—Ala—Ala—
Ala—Tyr—Xaa—Asn—

The enzyme has a molecular weight of 28.4 kDa, as determined by mass spectrometry.

Immunochemical Properties

In another preferred embodiment, the lipolytic enzyme of the invention is characterized by having having immunochemical properties identical or partially identical (i.e. at least partially identical) to those of a lipase obtained from the strain *Fusarium culmorum* CBS 513.94.

The immunochemical properties can be determined by immunological cross-reaction identity tests. The identity tests can be performed by the well-known Ouchterlony double immunodiffusion procedure or by tandem crossed immunoelectrophoresis according to I. M. Roitt; Immunology, Gower Medical Publishing (1985) or N. H. Axelsen; Handbook of Immunoprecipitation-in-Gel Techniques; Blackwell Scientific Publications (1983), chapters 5 and 14. The terms "immunochemical identity" (antigenic identity) and "partial immunochemical identity" (partial antigenic identity) are described in Axelsen, supra, chapters 5, 19 and 20, and in I. M. Roitt, supra, Chapter 6.

Monospecific antiserum for use in immunological tests can be raised, e.g. in rabbits, against the purified lipase of the invention, e.g. as described in Chapter 41 of N. H. Axelsen, supra, or Chapter 23 of N. H. Axelsen et al., A Manual of Quantitative Immunoelectrophoresis, Blackwell Scientific Publications (1973).

Preparation of the Lipolytic Enzyme

The lipolytic enzyme of the invention may be produced by cultivation of a strain of *Fusarium culmorum* in a suitable nutrient medium, containing carbon and nitrogen sources and inorganic salts, followed by recovery of the lipase. In a preferred embodiment, the lipase producing strain is the strain *Fusarium culmorum* CBS 513.94, or a mutant or a variant thereof.

The lipolytic enzyme may also be obtained by recombinant DNA-technology by methods known in the art per se, e.g. isolating a DNA fragment encoding the lipase, combining the DNA fragment with appropriate expression signal(s) in an appropriate vector, introducing the vector or parts thereof into an appropriate host, either as an autonomously replicating plasmid or integrated into the chromosome, cultivating the host organism under conditions leading to expression of the lipase, and recovering the lipase from the culture medium.

In preferred embodiments of the invention, the host organism is of bacterial origin, preferably a strain of *Escherichia coli,* or a strain of Bacillus, or a strain of Streptomyces, or of fungal origin, preferably a strain of Aspergillus, a strain of Neurospora, a strain of Fusarium, or a strain of Trichoderma, or a yeast cell, preferably a strain of Saccharomyces, or a strain of Kluyveromyces, or a strain of Hansenula, or a strain of Pichia.

After the cultivation, the lipolytic enzyme may be recovered and purified from the culture broth by conventional methods, such as hydrophobic chromatography, ion exchange chromatography or combinations thereof.

Lipolytic Activity

The lipolytic activity may be determined using tributyrine as substrate. This method is based on the hydrolysis of tributyrin by the enzyme, and the alkali consumption is registered as a function of time.

One Lipase Unit (LU) is defined as the amount of enzyme which, under is standard conditions (i.e. at 30.0° C.; pH 7.0; and tributyrine as substrate) liberates 1 $\mu$mol titratable butyric acid per minute. Gum Arabic is used as emulsifier.

A folder AF 95/5 describing this analytical method in more detail is available upon request to Novo Nordisk A/S, Denmark, which folder is hereby included by reference.

Detergent Compositions

The lipolytic enzyme of the invention may typically be a component of a detergent composition. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g. as powder, granules, paste or liquid. A liquid detergent may be aqueous, typically containing up to 70% water and 0–30% organic solvent, or nonaqueous.

The detergent composition comprises one or more surfactants, each of which may be anionic, nonionic, cationic, or zwitterionic. The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. It may also contain 0–40% of nonionic surfactant such as alcohol ethoxylate (AEO or AE), carboxylated alcohol ethoxylates, nonylphenol ethoxylate, alkylpolyglycoside, alkyldimethylamine oxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes conventionally used in detergent compositions, such as an amylase, a cutinase, a protease, a cellulase, a peroxidiase, and/or an oxidase.

The detergent may contain 1–65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethylcellulose (CMC), poly (vinylpyrrolidone) (PVP), polyethyleneglycol (PEG), poly (vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzenesulfonate (NOBS). Alternatively, the bleaching system may comprise peroxyacids of, e.g., the amide, imide, or sulfone type.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil-redeposition agents, dyes, bactericides, optical brighteners, or perfume.

The pH (measured in aqueous solution at use concentration) will usually be neutral or alkaline, e.g. in the range of 7–11.

Particular forms of detergent compositions within the scope of the invention include:

1) A detergent composition formulated as a granulate having a bulk density of at least 600 g/l comprising

| | |
|---|---|
| Linear alkylbenzenesulfonate (calculated as acid) | 7–12% |
| Alcohol ethoxysulfate (e.g. $C_{12-18}$ alcohol, 1–2 EO) or alkyl sulfate (e.g. $C_{16-18}$) | 1–4% |
| Alcohol ethoxylate (e.g. $C_{14-15}$ alcohol, 7 EO) | 5–9% |
| Sodium carbonate (as $Na_2CO_3$) | 14–20% |
| Soluble silicate (as $Na_2O,2SiO_2$) | 2–6% |
| Zeolite (as $NaA1SiO_4$) | 15–22% |
| Sodium sulfate (as $Na_2SO_4$) | 0–6% |
| Sodium citrate/citric acid (as $C_6H_5Na_3O_7/C_6H_8O_7$) | 0–15% |
| Sodium perborate (as $NaBO_3.H_2O$) | 11–18% |
| TAED | 2–6% |
| Carboxymethylcellulose | 0–2% |
| Polymers (e.g. maleic/acrylic acid copolymer, PVP, PEG) | 0–3% |
| Enzymes (calculated as pure enzyme protein) | 0.0001–0.1% |
| Minor ingredients (e.g. suds suppressors, perfume, optical brightener, photobleach) | 0–5% |

2) A detergent composition formulated as a granulate having a bulk density of at least 600 g/l comprising

| | |
|---|---|
| Linear alkylbenzenesulfonate (calculated as acid) | 6–11% |
| Alcohol ethoxysulfate (e.g. $C_{12-18}$ alcohol, 1–2 EO or alkyl sulfate (e.g. $C_{16-18}$) | 1–3% |
| Alcohol ethoxylate (e.g. $C_{14-15}$ alcohol, 7 EO) | 5–9% |
| Sodium carbonate (as $Na_2CO_3$) | 15–21% |
| Soluble silicate (as $Na_2O,2SiO_2$) | 1–4% |
| Zeolite (as $NaA1SiO_4$) | 24–34% |
| Sodium sulfate (as $Na_2SO_4$) | 4–10% |
| Sodium citrate/citric acid (as $C_6H_5Na_3O_7/C_6H_8O_7$) | 0–15% |
| Carboxymethylcellulose | 0–2% |
| Polymers (e.g. maleic/acrylic acid copolymer, PVP, PEG) | 1–6% |
| Enzymes (calculated as pure enzyme protein) | 0.0001–0.1% |
| Minor ingredients (e.g. suds suppressors, perfume) | 0–5% |

3) A detergent composition formulated as a granulate having a bulk density of at least 600 g/l comprising

| | |
|---|---|
| Linear alkylbenzenesulfonate (calculated as acid) | 5–9% |
| Alcohol ethoxylate (e.g. $C_{12-15}$ alcohol, 7 EO) | 7–14% |
| Soap as fatty acid (e.g. $C_{16-22}$ fatty acid) | 1–3% |
| Sodium carbonate (as $Na_2CO_3$) | 10–17% |
| Soluble silicate (as $NO,2SiO_2$) | 3–9% |
| Zeolite (as $NaA1SiO_4$) | 23–33% |
| Sodium sulfate (as $Na_2SO_4$) | 0–4% |
| Sodium perborate (as $NaBO_3.H_2O$) | 8–16% |
| TAED | 2–8% |
| Phosphonate (e.g. EDTMPA) | 0–1% |
| Carboxymethylcellulose | 0–2% |
| Polymers (e.g. maleic/acrylic acid copolymer, PVP, PEG) | 0–3% |
| Enzymes (calculated as pure enzyme protein) | 0.0001–0.1% |
| Minor ingredients (e.g. suds suppressors, Perfume, optical brightener) | 0–5% |

4) A detergent composition formulated as a granulate having a bulk density of at least 600 g/l comprising

| | |
|---|---|
| Linear alkylbenzenesulfonate (calculated as acid) | 8–12% |
| Alcohol ethoxylate (e.g. $C_{12-15}$ alcohol, 7 EO) | 10–25% |
| Sodium carbonate (as $Na_2CO_3$) | 14–22% |
| Soluble silicate (as $Na_2O,2SiO_2$) | 1–5% |
| Zeolite (as $NaA1SiO_4$) | 25–35% |
| Sodium sulfate (as $Na_2SO_4$) | 0–10% |
| Carboxymethylcellulose | 0–2% |
| Polymers (e.g. maleic/acrylic acid copolymer, PVP, PEG) | 1–3% |
| Enzymes (calculated as pure enzyme protein) | 0.0001–0.1% |
| Minor ingredients (e.g. suds suppressors, perfume) | 0–5% |

5) An aqueous liquid detergent composition comprising

| | |
|---|---|
| Linear alkylbenzenesulfonate (calculated as acid) | 15–21% |
| Alcohol ethoxylate (e.g. $C_{12-15}$ alcohol, 7 EO or $C_{12-15}$ alcohol, 5 EO) | 12–18% |
| Soap as fatty acid (e.g. oleic acid) | 3–13% |
| Alkenylsuccinic acid ($C_{12-14}$) | 0–13% |
| Aminoethanol | 8–18% |
| Citric acid | 2–8% |
| Phosphonate | 0–3% |
| Polymers (e.g. PVP, PEG) | 0–3% |
| Borate (as $B_4O_7$) | 0–2% |
| Ethanol | 0–3% |
| Propylene glycol | 8–14% |
| Enzymes (calculated as pure enzyme protein) | 0.0001–0.1% |
| Minor ingredients (e.g. dispersants, suds suppressors, perfume, optical brightener) | 0–5% |

6) An aqueous structured liquid detergent composition comprising

| | |
|---|---|
| Linear alkylbenzenesulfonate (calculated as acid) | 15–21% |
| Alcohol ethoxylate (e.g. $C_{12-15}$ alcohol, 7 EO, or $C_{12-15}$ alcohol, 5 EO) | 3–9% |
| Soap as fatty acid (e.g. oleic acid) | 3–10% |
| Zeolite (as $NaA1SiO_4$) | 14–22% |
| Potassium citrate | 9–18% |
| Borate (as $B_4O_7$) | 0–2% |
| Carboxymethylcellulose | 0–2% |
| Polymers (e.g. PEG, PVP) | 0–3% |
| Anchoring polymers such as, e.g., lauryl methacrylate/acrylic acid copolymer; molar ratio 25:1; MW 3800 | 0–3% |
| Glycerol | 0–5% |
| Enzymes (calculated as pure enzyme protein) | 0.0001–0.1% |
| Minor ingredients (e.g. dispersants, suds suppressors, perfume, optical brighteners) | 0–5% |

7) A detergent composition formulated as a granulate having a bulk density of at least 600 g/l comprising

| | |
|---|---|
| Fatty alcohol sulfate | 5–10% |
| Ethoxylated fatty acid monoethanolamide | 3–9% |
| Soap as fatty acid | 0–3% |
| Sodium carbonate (as $Na_2CO_3$) | 5–10% |
| Soluble silicate (as $Na_2O,2SiO_2$) | 1–4% |
| Zeolite (as $NaA1SiO_4$) | 20–40% |
| Sodium sulfate (as $Na_2SO_4$) | 2–8% |
| Sodium perborate (as $NaBO_3.H_2O$) | 12–18% |
| TAED | 2–7% |
| Polymers (e.g. maleic/acrylic acid copolymer, PEG) | 1–5% |
| Enzymes (calculated as pure enzyme protein) | 0.0001–0.1% |
| Minor ingredients (e.g. optical brightener, suds suppressors, perfume) | 0–5% |

8) A detergent composition formulated as a granulate comprising

| | |
|---|---|
| Linear alkylbenzenesulfonate (calculated as acid) | 8–14% |
| Ethoxylated fatty acid monoethanolamide | 5–11% |
| Soap as fatty acid | 0–3% |
| Sodium carbonate (as $Na_2CO_3$) | 4–10% |
| Soluble silicate (as $Na_2O,2SiO_2$) | 1–4% |
| Zeolite (as $NaA1SiO_4$) | 30–50% |
| Sodium sulfate (as $Na_2SO_4$) | 3–11% |
| Sodium citrate (as $C_6H_5Na_3O_7$) | 5–12% |
| Polymers (e.g. PVP, maleic/acrylic acid copolymer, PEG) | 1–5% |
| Enzymes (calculated as pure enzyme protein) | 0.0001–0.1% |
| Minor ingredients (e.g. suds suppressors, perfume) | 0–5% |

9) A detergent composition formulated as a granulate comprising

| | |
|---|---|
| Linear alkylbenzenesulfonate (calculated as acid) | 6–12% |
| Nonionic surfactant | 1–4% |
| Soap as fatty acid | 2–6% |
| Sodium carbonate (as $Na_2CO_3$) | 14–22% |
| Zeolite (as $NaA1SiO_4$) | 18–32% |
| Sodium sulfate (as $Na_2SO_4$) | 5–20% |
| Sodium citrate (as $C_6H_5Na_3O_7$) | 3–8% |
| Sodium perborate (as $NaBO_3.H_2O$) | 4–9% |
| Bleach activator (e.g. NOBS or TAED) | 1–5% |
| Carboxymethylcellulose | 0–2% |
| Polymers (e.g. polycarboxylate or PEG) | 1–5% |
| Enzymes (calculated as pure enzyme protein) | 0.0001–0.1% |
| Minor ingredients (e.g. optical brightener perfume) | 0–5% |

10) An aqueous liquid detergent composition comprising

| | |
|---|---|
| Linear alkylbenzenesulfonate (calculated as acid) | 15–23% |
| Alcohol ethoxysulfate (e.g. $C_{12-15}$ alcohol, 2–3 EO) | 8–15% |
| Alcohol ethoxylate (e.g. $C_{12-15}$ alcohol, 7 EO, or $C_{12-15}$ alcohol, 5 EO) | 3–9% |
| Soap as fatty acid (e.g. lauric acid) | 0–3% |
| Aminoethanol | 1–5% |
| Sodium citrate | 5–10% |
| Hydrotrope (e.g. sodium toluensulfonate) | 2–6% |
| Borate (as $B_4O_7$) | 0–2% |

-continued

| | |
|---|---|
| Carboxymethylcellulose | 0–1% |
| Ethanol | 1–3% |
| Propylene glycol | 2–5% |
| Enzymes (calculated as pure enzyme protein) | 0.0001–0.1% |
| Minor ingredients (e.g. polymers, dispersants, perfume, optical brighteners) | 0–5% |

11) An aqueous liquid detergent composition comprising

| | |
|---|---|
| Linear alkylbenzenesulfonate (calculated as acid) | 20–32% |
| Alcohol ethoxylate (e.g. $C_{12-15}$ alcohol, 7 EO, or $C_{12-15}$ alcohol, 5 EO) | 6–12% |
| Aminoethanol | 2–6% |
| Citric acid | 8–14% |
| Borate (as $B_4O_7$) | 1–3% |
| Polymer (e.g. maleic/acrylic acid copolymer, anchoring polymer such as, e.g., lauryl methacrylate/acrylic acid copolymer) | 0–3% |
| Glycerol | 3–8% |
| Enzymes (calculated as pure enzyme protein) | 0.0001–0.1% |
| Minor ingredients (e.g. hydrotropes, dispersants, perfume, optical brighteners) | 0–5% |

12) A detergent composition formulated as a granulate having a bulk density of at least 600 g/l comprising

| | |
|---|---|
| Anionic surfactant (linear alkylbenzene-sulfonate, alkyl sulfate, alpha-olefinsulfonate, alpha-sulfo fatty acid methyl esters, alkanesultonates, soap) | 25–40% |
| Nonionic surfactant (e.g. alcohol ethoxylate) | 1–10% |
| Sodium carbonate (as $Na_2CO_3$) | 8–25% |
| Soluble silicates (as $Na_2O$, $2SiO_2$) | 5–15% |
| Sodium sulfate (as $Na_2SO_4$) | 0–5% |
| Zeolite (as $NaA1SiO_4$) | 15–28% |
| Sodium perborate (as $NaBO_3.4H_2O$) | 0–20% |
| Bleach activator (TAED or NOBS) | 0–5% |
| Enzymes (calculated as pure enzyme protein) | 0.0001–0.1% |
| Minor ingredients (e.g. perfume, optical brighteners) | 0–3% |

13) Detergent formulations as described in 1)–12) wherein all or part of the linear alkylbenzenesulfonate is replaced by ($C_{12}$–$C_{18}$) alkyl sulfate.

14) A detergent composition formulated as a granulate having a bulk density of at least 600 g/l comprising

| | |
|---|---|
| ($C_{12}$—$C_{18}$) alkyl sulfate | 9–15% |
| Alcohol ethoxylate | 3–6% |
| Polyhydroxy alkyl fatty acid amide | 1–5% |
| Zeolite (as $NaA1SiO_4$) | 10–20% |
| Layered disilicate (e.g. SK56 from Hoechst) | 10–20% |
| Sodium carbonate (as $Na_2CO_3$) | 3–12% |
| Soluble silicate (as $Na_2O,2SiO_2$) | 0–6% |
| Sodium citrate | 4–8% |
| Sodium percarbonate | 13–22% |
| TAED | 3–8% |
| Polymers (e.g. polycarboxylate and PVP = | 0–5% |
| Enzymes (calculated as pure enzyme protein) | 0.0001–0.1% |
| Minor ingredients (e.g. optical brightener, photo bleach, perfume, suds suppressors) | 0–5% |

15) A detergent composition formulated as a granulate having a bulk density of at least 600 g/l comprising

| | |
|---|---|
| ($C_{12}$—$C_{18}$) alkyl sulfate | 4–8% |
| Alcohol ethoxylate | 11–15% |
| Soap | 1–4% |
| Zeolite MAP or zeolite A | 35–45% |
| Sodium carbonate (as $Na_2CO_3$) | 2–8% |
| Soluble silicate (as $Na_2O,2SiO_2$) | 0–4% |
| Sodium percarbonate | 13–22% |
| TAED | 1–8% |
| Carboxymethyl cellulose | 0–3% |
| Polymers (e.g. polycarboxylates and PVP) | 0–3% |
| Enzymes (calculated as pure enzyme protein) | 0.0001–0.1% |
| Minor ingredients (e.g. optical brightener, phosphonate, perfume) | 0–3% |

16) Detergent formulations as described in 1)–15) which contain a stabilized or encapsulated peracid, either as an additional component or as a substitute for already specified bleach systems.

17) Detergent compositions as described in 1), 3), 7), 9) and 12) wherein perborate is replaced by percarbonate.

18) Detergent compositions as described in 1), 3), 7), 9), 12), 14) and 15) which additionally contain a manganese catalyst. The manganese catalyst may, e.g., be one of the compounds described in "Efficient manganese catalysts for low-temperature bleaching", *Nature* 369, 1994, pp. 637–639.

19) Detergent composition formulated as a nonaqueous detergent liquid comprising a liquid nonionic surfactant such as, e.g., linear alkoxylated primary alcohol, a builder system (e.g. phosphate), enzyme and alkali. The detergent may also comprise anionic surfactant and/or a bleach system.

The lipolytic enzyme of the invention may be incorporated in concentrations conventionally employed in detergents. It is at present contemplated that, in the detergent composition of the invention, the lipase may be added in an amount corresponding to 0.001–100 mg of lipase per liter of wash liquor.

EXAMPLES

The invention is further illustrated with reference to the following examples which are not intended to be in any way limiting to the scope of the invention as claimed.

Example 1

Cultivation Example

Seed cultures of the strain *Fusarium culmorum* CBS 513.94 were produced in 500 ml shakeflasks containing 100 ml of the following composition:

Corn steep liquer (dried) 12 g/l

Glucose 24 g/l

To each flask is added 0.5 g $CaCO_3$ and 0.5 ml of oil.

pH is adjusted to 5.5 before autoclavation.

After 3 days at 26° C. and 250 rpm, 5 ml of each of the seed cultures were inoculated in shakeflasks containing 100 ml of the following medium:

Pepton, Difco 0118 6 g/l

Pepticase, Sheffield Products 4 g/l

Yeast extract, Difco 0127 3 g/l

Meat extract, Difco 0126 1.5 g/l

Dextrose, Roquette 101-0441 1 g/l

Olive oil, Sigma 10 g/l pH is adjusted to 7.3–7.4 before autoclavation.

Cultivation took place for 9 days at 26° C. and 250 rpm. The broths were centrifuged and the supernatants purified on a hydrophobic matrix (TSK gel Butyl-ToyoPearl 650 C column, available from Tosoh Corporation, Japan), and applied for further studies.

Example 2

Characterization Example pH Optimum

The supernatant obtained according to Example 1 was subjected to the LU method for determining lipase activity described above, and the relation between pH and lipase activity of the lipolytic enzyme of the invention was determined at 30° C. in the range of from pH 6 to pH 10.

The results of this characterization is presented in FIG. 1. The lipolytic enzyme has its pH optimum in the range of from about pH 7 to about pH 9, more specifically around pH 8.

Molecular Weight Determination

Mass spectrometry was done using matrix assisted laser desorption ionisation time-of flight (MALDI-TOF) mass spectrometry in a VG Analytical TofSpec. For mass spectrometry, 2 μl of sample obtained according to Example 1 were mixed with 2 μl saturated matrix solution (α-cyano-4-hydroxycinnamic acid in 0.1% TFA:acetonitrile (70:30)), and 2 μl of the mixture spotted onto the target plate. Before introduction into the mass spectrometer the solvent was removed by evaporation. The sample was desorbed and ionised by 4 ns laser pulses (337 nm) at threshold laser power and accelerated into the field-free flight tube by an accelerating voltage of 25 kV. Ions were detected by a micro channel plate set at 1850 V. The spectra were calibrated externally with proteins of known mass.

A mass of 28.4 kDa was determined.

N-terminal Amino Acid Sequence

Using standard methods for obtaining and sequencing peptides [Findlay & Geisow (Eds.) (1989); Protein sequencing—a practical approach; IRL Press], the following 25 N-terminal amino acid residues of the lipolytic enzyme have been identified, as presented by SEQ ID NO:1 (where Xaa designates an unknown amino acid residue):

Ala—Val—Ser—Val—Ser—Thr—Thr—Asp—Phe—Gly—Asn—
Phe—Lys—Phe—Tyr—Ile—Gln—His—Gly—Ala—Ala—
Ala—Tyr—Xaa—Asn—

Example 3

Lipolytic Activity

Using a monolayer equipment (KSV-5000, KSV Instruments, Finland) it has been demonstrated that the lipolytic enzyme from *Fusarium culmorum* has considerably increased activity towards dicaprin in presence of long chained alcoholethoxylates.

A mixed monolayer in a well defined overall composition, made of a diglyceride substrate and a monocomponent alcoholethoxylate (AEO: Heptaethylene glycol monooctadecyl ether) is spread on an aqueous subphase (10 mM Glycine, pH 10.0, 0.1 mM EDTA, 25° C.). The surface pressure is adjusted to the desired value, and a well-defined amount of enzyme (10 LU; lipase units as defined above) is injected into the subphase. Lipolytic action is manifested through the speed of a mobile barrier compressing the monolayer in order to maintain constant surface pressure as insoluble substrate molecules are hydrolysed into more water soluble reaction products. Using this assay, lipolytic enzymes are discriminated by a parameter β indicating the final area-fraction of substrate (dicaprin) left unhydrolysed by the enzyme as lipolytic activity stops.

In this way, the lipase of the invention was compared to an Aspergillus lipase conventionally used in detergents (Lipolase™, available from Novo Nordisk A/S, Denmark). The results are presented in Table 1, below.

TABLE 1

Improved tolerance of lipolytic enzyme from *Fusarium culmorum* compared to Lipolase ™.

| | β(30 mN/m)* |
|---|---|
| Lipolase ™ | 57% |
| *Fusarium culmorum* lipase | 25% |

*Surface pressure employed.

These results show that when compared to Lipolase™, the lipolytic enzyme obtained from *Fusarium culmorum* is considerably more efficient when alcoholethoxylates are present in the substrate phase.

Example 4

Substrate Affinity

A procedure has been developed aiming at a simple comparison of the ability of lipolytic enzymes to accumulate on/in a substrate phase (olive oil) at alkaline pH (pH 9.0) and presence of the non-ionic surfactant Dobanol 25-7 (2500 ppm) in the aqueous phase.

Procedure

1. Two identical buffer solutions (5 ml) are prepared in 20 ml sealable vials, (“Sample” (s) and “Reference” (r)).
2. Enzyme is added into “Sample” and “Reference” and the lipase concentration is determined (X LU/ml).
3. Olive oil is added onto the “Sample” and both lipase solutions are shaken vigorously. Incubation at 4° C. over night.
4. Remaining lipase concentration in the aqueous phases is determined after incubation ($Y_1$ LU/mi; i=r,s).

Summary of Incubation Conditions

Buffer 100 mM Glycine (5 ml).

pH 9.0.

Substrate Olive oil (5 ml).

Temperature 4° C.

Lipase activity 5–10 LU/ml.

Incubation Over night (24–26 hours).

Evaluation of Data

The result is calculated by comparing the activity-loss upon incubation in the aqueous phase in contact with olive oil to the activity-loss in the aqueous phase in absence of olive oil:

$$\alpha = Y_s / Y_f \text{ (see above)}$$

The results are presented in Table 2, below.

TABLE 2

Substrate Affinity

| Lipolytic Enzyme | α(%) |
|---|---|
| Lipolase ™ | 99% |
| *Fusarium culmorum* lipase | 99% |

We claim:

1. A lipolytic enzyme having immunochemical properties at least partially identical to those of a lipase obtained from the strain *Fusarium culmorum* CBS 513.94, which enzyme has the N-terminal amino acid sequence shown in SEQ ID NO: 1, in which Xaa denotes any amino acid residue.

2. The lipolytic enzyme of claim 1, which is obtained from a strain of *Fusarium culmorum.*

3. The lipolytic enzyme of claim 1, which is obtained from the strain *Fusarium culmorum* CBS 513.94, or a mutant or a variant thereof.

4. The lipolytic enzyme of claim 1, which has a pH optimum in the range of from about pH 7 to about pH 9, when determined at 30° C. with tributyrine as substrate.

5. The lipolytic enzyme of claim 1, which has a molecular weight of 28.4 kDa, as measured by SDS-PAGE.

6. A process for the preparation of the lipolytic enzyme of claim 1, which process comprises cultivation of a lipase producing strain of *Fusarium culmorum* in a suitable nutrient medium, containing carbon and nitrogen sources and other inorganic salts, followed by recovery of the lipolytic enzyme.

7. A detergent composition comprising the lipolytic enzyme of claim 1.

8. The detergent composition of claim 7, which further comprises at least one other enzyme.

9. The detergent composition of claim 8, wherein the other enzyme is a protease, an amylase, a cellulase, an oxidase or a peroxidase.

10. A detergent additive comprising the lipolytic enzyme of claim 1, provided in the form of a granulate, a liquid, a slurry or a protected enzyme.

11. The detergent additive of claim 10, wherein the granulate is a non-dusting granulate and the liquid is a stabilized liquid.

* * * * *

UNITED STATES PATENT AND TRADEMARK OFFICE
CERTIFICATE OF CORRECTION

PATENT NO. : 5,830,736
DATED : November 3, 1998
INVENTOR(S) : Oxenbøll, et al.

It is certified that error appears in the above-identified patent and that said Letters Patent is hereby corrected as shown below:

Col. 2, line 30: delete "muant" and insert --mutant--
Col. 5, line 65: delete "NO" and insert --$Na_2O$--
Col. 8, line 34: delete "alkanesultonates" and insert --alkanesulfonates--

Signed and Sealed this

Eighteenth Day of January, 2000

*Attest:*

Q. TODD DICKINSON

*Attesting Officer* *Commissioner of Patents and Trademarks*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 25 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

```
Ala Val Ser Val Ser Thr Thr Asp Phe Gly Asn Phe Lys Phe Tyr Ile
 1               5                   10                  15

Gln His Gly Ala Ala Ala Tyr Xaa Asn
            20                  25
```